United States Patent [19]

Walthall et al.

[11] Patent Number: 4,902,295

[45] Date of Patent: Feb. 20, 1990

[54] TRANSPLANTABLE ARTIFICIAL TISSUE

[75] Inventors: Bennie J. Walthall, El Sobrante; Yvonne E. McHugh, Berkeley; Houston F. Voss, Pleasanton, all of Calif.

[73] Assignee: Hana Biologics, Inc., Alameda, Calif.

[21] Appl. No.: 118,280

[22] Filed: Nov. 6, 1987

Related U.S. Application Data

[63] Continuation of Ser. No. 770,027, Aug. 26, 1985, abandoned.

[51] Int. Cl.$^4$ ................................................ A61F 2/02
[52] U.S. Cl. .......................................... 623/11; 623/66; 623/12; 435/178; 424/95; 424/110
[58] Field of Search ................... 435/178, 180, 182; 424/94.21, 95; 623/11, 66, 12

[56] References Cited

U.S. PATENT DOCUMENTS 4,645,669  2/1987  Reid ........................................ 424/95
4,722,898  2/1988  Errede et al. .......................... 435/182

OTHER PUBLICATIONS

Bell et al., "Reconstruction of a Thyroid Gland Equivalent from Cells and Matrix Materials", *J. Exp. Zool.*, 232:277–285, (1984).

*Primary Examiner*—Alan W. Cannon
*Attorney, Agent, or Firm*—William B. Walker; Laura Terlizzi

[57] ABSTRACT

A transplantable artificial tissue matrix structure containing viable cells which is suitable for insertion into the body is made by polymerizing precursors in an aqueous solution to form a shape retaining solid matrix comprising viable cells, matrix polymer and reversible gel polymer. The solution contains a matrix polymer precursor, a reversible gel polymer precursor, and viable cells. The reversible gel polymer is dissolved and removed to yield an insoluble, porous matrix containing viable cells. The conditions and reagents are selected to maintain the viability of the cells. The invention is particularly suitable for artificial transplant matrix tissue containing pancreatic islet cells.

7 Claims, No Drawings

TRANSPLANTABLE ARTIFICIAL TISSUE

RELATIONSHIP TO COPENDING APPLICATION

This application is a continuation of copending application Ser. No. 770,027 filed Aug. 26, 1985, now abandoned.

FIELD OF THE INVENTION

This invention relates to an artificial tissue composition for insertion into the body and to the process for preparing it. In particular, this invention relates to a matrix composition containing cells which can be inserted to introduce the cells into the body and to the process of preparing this matrix. In one particular aspect, this invention relates to preparation of a matrix containing pancreatic B-cells which, when inserted into the body, can function as an artificial pancreas, introducing insulin produced by the B-cells cells into the body as needed.

BACKGROUND OF THE INVENTION

Insertion of a missing cell type into the body can be accomplished by implantation, transplantation or injection of cells. The cells can be in the form of tissue fragments, clumps of cells or single cells derived from the fragmentation of organs or tissues. Alternatively, the cells can be clumps of cells or single cells derived from cell culture, tissue culture or organ culture. If the cell insertion is to be successful, however, the cells must have the physiological environment after insertion which is required for the reorganization, growth or differentiation necessary to permit normal functioning in the body. The cells inserted into the body must be maintained in a physical relationship which permits adaptation to the new environment and promotes the changes which are required before normal cell functioning can occur.

Diabetes mellitis is an example of a disease state associated with an insufficiency or absence of certain types of cells in the body. In this disease, pancreatic B-cells are missing or deficient. The condition can be ameliorated by the successful insertion of the missing pancreatic B-cells.

Prior to this invention, attempts to introduce such cells into the body have not achieved the natural reorganization, growth or differenteration needed for optimum cell functioning in the body.

DESCRIPTION OF THE PRIOR ART

Prior art processes for inserting cells have been generally unsuccessful, primarily because they have not satisfied the cellular requirements of transplantation. Attempted matrix approaches have failed to form the matrix rapidly and without cellular damage. They have failed to provide shape and size control, the cell density required for proliferation, the matrix porosities for diffusion of nutrients and macromolecules, or the environment effecting cell-to-cell contact while permitting cell movement during tissue development.

U.S. Pat. No. 4,352,883 describes a process for encapsulating biological materials including cells in a semipermeable spherical membrane with a predetermined porosity. Although some size and shape control is possible with a membrane envelope, cell-to-cell contact, if present, is incidental and uncontrolled. U.S. Pat. 4,391,909 is directed to the improvement of a semipermeable membrane envelope, similar to U.S. Pat. No. 4,352,883, but with the addition of collagen within the membrane envelope for cell anchorage. The semipermeable membrane in these patents is designed to prevent macromolecules and cells outside the envelope from reaching the cells enclosed within the membrane envelope. Other related patents include U.S. Pat. Nos. 4,251,387, 4,324,683, 4,407,957, and 4,495,288. U.S. Pat. No. 4,487,758 refines the process, teaching refinements of the older processes, optimizing water content of the hydrogel, viscosity of the alginate solution and the use of two polymer layers for forming the membrane envelope. Cell-to-cell contact is again not promoted; the matrix is dissolved to permit the cells to float freely within the membrane enclosure. The primary object of the process and composition of the above patents is to enclose cells in a protective enveloping membrane which prevents cells and macromolecules having a molecular weight averaging more than 200,000 daltons in the external environment from reaching the cells in the envelope.

In contrast, an object of this invention is to provide a matrix in which the individual cells are supported, confined, anchored and nurtured. The matrix can be manufactured to provide any desired pore size, and in some embodiments, the matrix pores can be of such a size as to exclude cells and molecules from the external environment. In the preferred embodiments of this invention, the matrix is constructed to facilitate host cellular processes such as angiogenesis and facilitate transport of macromolecules and host cells throughout the matrix.

U.S. Pat. No. 4,353,888 also describes a process for encapsulating mammalian cells within a semipermeable polymeric membrane to prevent immune rejection of the cells by antibody or immune cells of the recipient. The process involves dispersing an aqueous dispersion of the cells in a water-in-oil emulsion and coating the aqueous droplets with the polymer. Shape is limited to small spheres, size control is poor, cell-to-cell contact is not effected, and no matrix is provided within the spheres.

Bell. E. et al. *J.Experimental Zoology.* 232:277–285 (1984) describe a process for enclosing thyroid cells in a collagen matrix which contracts around the cells to produce an artificial thyroid gland for implantation. Bell et al do not achieve the cell-to-cell contact required for optimum implantation, although some cell-to-cell contact could be achieved if the number of cells used was sufficiently high. However, no shape, size or porosity control is possible with the Bell et al system. Other publications applying this procedure to skin grafting are Bell, E. et al. *J.Invest.Dermatol.* 81:2s–10s (1983); Hull, B. et al. *J.Invest.Dermatol.* 81:429–436 (1983); Bell, E. et al. *Proc.Natl.Acad.Sci.* 76:1274–1278 (1979); Hull, B. et al. *J.Invest.Dermatol.* 81:436–438 (1983); and U.S. Pat. No. 4,485,096.

Nilsson, K. et al. *Eur.J.Appl.Microbiol.Biotech.* 17:319–326 (1983) describes a process for immobilizing viable cells in various monomers or polymers dispersed as a water-in-oil emulsion during matrix formation. The process yields only spherical particles and limited ability to control particle size. Polymer forming materials tested by Nilsson et al include fibrin, alginates, polyacrylamides and other materials. No size or shape control is provided.

U.S. Pat. No. 4,458,678 describes a wound healing product. Viable cells are introduced into a fibrous lattice which has some of the attributes required for an insertable matrix. However, no shape or size control is provided.

U.S. Pat. No. 4,349,530 describes incorporating biologically active substances into cross-linked albumin particles. This process is not suitable for cells, and even if modified to accommodate cells, would not provide the cell-to-cell contact or control of size, shape or porosity required for cellular insertion.

SUMMARY OF THE INVENTION

The cell containing matrix of this invention is prepared by
(1) effecting polymerization of matrix and reversible gel precursors in an aqueous mixture of
  (a) viable cells to be incorporated into a matrix,
  (b) matrix precursor, and
  (c) reversible gel precursor to yield an insoluble matrix;
(2) separating the insoluble matrix from the polymerization promoting solution;
(3) effecting solubilization of gel polymer in the insoluble matrix; and
(4) recovering an insoluble, porous matrix containing viable cells, wherein the solution ingredients, reagents used to effect the polymerization and/or dissolution, and the temperatures are selected to maintain viability of the cells. Depending upon the selection of matrix precursor and reversible gel precursor, the polymerization can be effected by exposing the respective precursor to a polymerization promoting reagent and/or a polymerization promoting condition. Likewise, depending upon the nature of the reversible gel polymer, the dissolution of the gel polymer component of the matrix can be effected by choice of a suitable chemical composition or other condition of the solution in which the matrix is surrounded.

The cell containing matrix of this invention comprises viable cells incorporated into a porous matrix of a non-toxic, cell compatible polymer, the matrix having the porosity required for cell movement and the cell-to-cell contact required for growth and reorganization to permit normal functioning after insertion into the body.

The cell containing matrix intermediate of this invention comprises viable cells incorporated into a solid matrix of matrix polymer and reversible gel polymer, the cells having the cell-to-cell contact required for growth after dissolution of the reversible gel polymer.

DETAILED DESCRIPTION OF THE INVENTION

For a cell implant or other type of viable cell insert to be effective, the cells must undergo any reorganization, growth and differentiation which is required to permit the cells to achieve normal functioning in the body. For a three-dimensional matrix holding the cells in a unitary mass to promote this result, it should satisfy all of the following criteria. The process used for forming the matrix must be rapid and sufficiently gentle to prevent cellular damage. The materials used must permit a rapid reaction under these gentle conditions. The process should allow shape and size control. For a process to be generally applicable for a variety of cells, it should produce shapes having controllable final cell densities ranging from particles containing one to a few cells to shapes containing cells at a density approaching the cell density in tissue, i.e. approximately from $10^9$–$10^{10}$ cells/cc.

The ranges of size of the particles should be selected to promote cell viability in a physiological environment. Soon after implantation, diffusion of oxygen and nutrients into the central interior of particles having excessive diameters would be insufficient, causing death of cells in the central interior. However, if the particle diameters are very small, the particles (and the cells enclosed in their matrix) may be successfully attacked by humoral or cellular components of the host immune system. Since with increasing diameters, surface areas of particles increase more slowly than enclosed volumes, larger particles would be more resistant to such attacks. Thus the particle size must be selected to balance these factors. The particle sizes are thus limited to a size of from 20 to 5000 microns and are preferably within a range of from 50 to 1000 microns. The optimum particle size is within the range of from 100 to 500 microns.

The final matrix must be nontoxic and biocompatible, and it can be biodegradable. The process should provide the ability to vary and control the matrix porosity to the level necessary to permit the requisite diffusion of nutrients and macromolecules. The process should be able to provide matrices which partially immobilize the cells to encourage cell-to-cell contact while being sufficiently loose to permit cell movement which may be necessary for rearrangement during tissue development. The matrix composition should also be susceptable to the degradation, removal or alteration in the host environment which is required for entry of the host cells into the matrix during the vascularization process. These criteria can be satisfied with the process and composition of this invention.

The first step of the process of this invention comprises contacting a first aqueous solution containing cells and polymer precursors with a second aqueous polymerization promoting solution until a solid matrix of matrix polymer and reversible gel polymer containing cells is formed. The polymer precursors include a matrix precursor and a reversible gel precursor.

Matrix precursors are water-soluble compounds and compositions which can be polymerized to form a solid matrix within which cells can achieve the reorganization, growth and/or differenteration required for successful adaptation. They must form a matrix structure which is sufficiently stable to substantially retain its configuration after reversible gel polymer is removed to leave a porous structure. They must be non-toxic, biocompatible and can be biodegradable. They must undergo the polymerization to form the solid, insoluble structure under conditions which do not interfere with polymerization of the reversible gel precursor, and must remain insoluble under conditions wherein the reversible gel polymer can be solubilized.

The preferred matrix precursors yield polymers which undergo spacial contraction during polymerization. These preferred matrix precursors are capable of bringing cells into closer proximity during polymerization, increasing cell-to-cell contact.

Examples of suitable matrix precursors and the reagents and/or temperature conditions effecting polymerization are listed in Table A.

TABLE A

| Matrix Polymer | Promoter |
|---|---|
| Plasma | Endogenous Thrombin via |
| $Ca^{+2}$ | Activation[b] |
| Fibrinogen | Thrombin[a] |
| Casein | Renin/pepsin[a] |
| Fibrin | Factor XIII(a)[a] |
| Limulus lysate | Endotoxin[a] |
| Milk protein | Renin/pepsin[a] |
| Collagen, all types (I, II and III) | Elevated temperature at neutral pH[b] |

[a]Promoter is provided in the first solution
[b]Promoter is provided in a second solution When the matrix precursor is plasma, the matrix polymerization promoter is introduced in the second solution with the gel precursor polymerization promoter. When the matrix precursor is collagen, the polymerization is effected by elevated temperature of the second solution containing the gel precursor polymerization promoter.

The reversible gel precursors must also be water-soluble, non-toxic and biocompatible. Additionally, they should rapidly polymerize or gel to form a solid structure under conditions which do not interfere with the polymerization of the matrix precursor to form the matrix polymer. Furthermore, the gel polymer must be susceptable to depolymerization or dissolution under conditions which will not significantly affect the structure of the matrix polymer or cell viability. The function of the gel polymer in the composition is to form an integral structure with the cells and matrix polymer which, when removed, will leave a pore structure in the matrix. The pore structure, while leaving the cells partially immobilized, should allow sufficient cell movement for rearrangement during tissue development, as well as permitting diffusion of nutrients and macromolecules to and from the cells.

The gel polymer precursors are gelled by reagent and/or temperature conditions in the second solution.

Examples of suitable gel precursors, the conditions and/or reagents promoting polymerization, and the agents and/or conditions effecting dissolution are listed in Table B.

TABLE B

| Gel Polymer Precursor | Promoter[b] | Dissolution Agent |
|---|---|---|
| Alginate | $Ca^{+2}$ | Citrate |
| Gums[a] | $Ca^{+2}$ | Citrate |
| Agarose | Low Temp. | Temp. elevation or agarase |

[a]Carrageenan, agar, guar gum, gum arabic, pectins, tragacanth gum, xanthan gum, etc.
[b]Promoter provided in a second solution.

The aqueous solution for the matrix precursor and the reversible gel precursor must be free from compounds which promote polymerization of either before the shape of the product is determined. It must also provide a non-toxic, biocompatible environment for the cells.

In general, the first solution is prepared immediately before being introduced into the second solution, and the shape of the product is determined by interactions of the reagents and/or temperature of the second solution with the reactants in the first solution. The gel polymer precursor rapidly polymerizes to form an initial shape, and the matrix polymer forms later, retaining this shape. By having the gel polymer promoting conditions and/or reagents present in the second solution, shape formation occurs immediately upon introduction of the first solution into the second solution.

The first solution should be an isotonic solution with a pH which does not significantly impair cell viability during particle formation. Preferably, the solution is an isotonic saline solution or tissue culture medium of the type which is commonly used in cell and tissue cultures. Suitable isotonic saline solutions include Hank's Balanced Salt Solution and Earle's Balanced Salt Solution. Suitable tissue media include Dulbecco's Minimal Essential Medium or RPMI 1640 medium. These formulations are set forth in the following tables.

TABLE C

Earl's Balanced Salt Solution

| Components | Concentration, mg/liter |
|---|---|
| Inorganic salts | |
| $CaCl_2$ (anhydrous) | 200.00 |
| KCl | 400.00 |
| $MgSO_4$ (anhydrous) | 97.70 |
| NaCl | 6800.00 |
| $NaHCO_3$ | 2200.00 |
| $NaH_2PO_4 \cdot H_2O$ | 140.00 |
| Other Components | |
| Glucose | 1000.00 |
| Phenol Red | 10.00 |

TABLE D

Hank's Balanced Salt Solution

| Components | Concentration, mg/liter |
|---|---|
| Inorganic salts | |
| $CaCl_2$ (anhydrous) | 140.00 |
| KCl | 400.00 |
| $KH_2PO_4$ | 60.00 |
| $MgSO_4$ (anhydrous) | 97.70 |
| NaCl | 8000.00 |
| $NaHCO_3$ | 350.00 |
| $Na_2HPO_4$ (anhydrous) | 48.00 |
| Other Components | |
| Glucose | 1000.00 |
| Phenol Red | 10.00 |

TABLE E

Dulbecco's Minimal Essential Medium

| Components | Concentration, mg/liter |
|---|---|
| Inorganic salts | |
| $CaCl_2$ (anhydrous) | 200.00 |
| $Fe(NO_3)_3 \cdot 9H_2O$ | 0.10 |
| KCl | 400.00 |
| $MgSO_4$ (anhydrous) | 97.70 |
| NaCl | 6400.00 |
| $NaHCO_3$ | 3700.00 |
| $NaH_2PO_4 \cdot H_2O$ | 125.00 |
| Other Components | |
| Glucose | 1000.00 |
| Phenol Red | 15.00 |
| Sodium pyruvate | 110.00 |
| Amino Acids | |
| L-Arginine-HCl | 84.00 |
| L-Cystine-2HCl | 62.59 |
| L-Glutamine | 584.00 |
| Glycine | 30.00 |
| L-Histidine-HCl.$H_2O$ | 42.00 |
| L-Isoleucine | 104.80 |
| L-Leucine-HCl | 104.80 |
| L-Lysine-HCl | 146.50 |
| L-Methionine | 30.00 |
| L-Phenylalanine | 66.00 |
| L-Serine | 42.00 |
| L-Threonine | 95.20 |
| L-Tryptophan | 16.00 |
| L-Tyrosine | 72.00 |
| L-Valine | 93.60 |

TABLE E-continued

Dulbecco's Minimal Essential Medium

| Components | Concentration, mg/liter |
|---|---|
| Vitamins | |
| D-Calcium pantothenate | 4.00 |
| Choline chloride | 4.00 |
| Folic acid | 4.00 |
| i-Inositol | 7.00 |
| Nicotinamide | 4.00 |
| Pyridoxal-HCl | 4.00 |
| Riboflavin | 0.40 |
| Thiamine-HCl | 4.00 |

TABLE F

Modified RPMI 1640 Medium

| Components | Concentration, mg/liter |
|---|---|
| Inorganic salts | |
| $Ca(NO_3)_2.4H_2O$ | 100.00 |
| KCl | 400.00 |
| $MgSO_4$ (anhydrous) | 48.90 |
| NaCl | 6000.00 |
| $NaHCO_3$ | 2000.00 |
| Other Components | |
| Glucose | 2000.00 |
| Glutathione (reduced) | 1.00 |
| Phenol Red | 5.00 |
| Amino Acids | |
| L-Arginine (free base) | 200.00 |
| L-Asparagine (anhydrous) | 50.00 |
| L-Aspartic acid | 20.00 |
| L-Cystine.2HCl | 65.20 |
| L-Glutamic acid | 20.00 |
| L-Glutamine | 300.00 |
| Glycine | 10.00 |
| L-Histidine (free base) | 15.00 |
| Hydroxy-L-proline | 20.00 |
| L-Isoleucine | 50.00 |
| L-Leucine | 50.00 |
| L-Lysine-HCl | 40.00 |
| L-Methionine | 15.00 |
| L-Phenylalanine | 15.00 |
| L-Proline | 20.00 |
| L-Serine | 30.00 |
| Amino acids | |
| L-Threonine | 20.00 |
| L-Tryptophan | 5.00 |
| L-Tyrosine | 20.00 |
| L-Valine | 20.00 |
| Vitamins | |
| p-Aminobenzoic acid | 1.00 |
| d-Biotin | 0.20 |
| D-Calcium pantothenate | 0.25 |
| Choline chloride | 3.00 |
| Folic acid | 1.00 |
| i-Inositol | 35.00 |
| Nicotinamide | 1.00 |
| Pyridoxine-HCl | 1.00 |
| Riboflavin | 0.20 |
| Thiamine-HCl | 1.00 |
| Vitamin $B_{12}$ | 0.005 |

The solution pH can be from 5 to 9 and is preferably from 6 to 8. The optimum pH is from 6.8 to 7.6.

The concentration of the matrix precursor and reversible gel precursor in the solution are selected to provide the desired pore structure and rigidity, and cell attachment.

The concentration of matrix precursor for most matrices can be from 1 microgram/ml to 100 mg/ml, preferably from 50 microgram/ml to 20 mg/ml and optimally from 0.1 mg/ml to 6 mg/ml. Other ranges may be preferred and optimum for matrices having different matrix strengths, rigidity and different cell attachment characteristics.

The reversible gel precursor concentration determines the degree of porosity. It should be selected to yield the porosity required to permit adequate flow of nutrients and macromolecules, and when necessary, to permit sufficient cell movement for reorganization. It can be from 1 microgram/ml to 100 mg/ml. For low porosity compositions, it is preferably from 1microgram/ml to 1 mg/ml, and for high porosity compositions, it is preferably from 1 to 100 mg/ml.

The terms "cell" and "cells", are defined for the purposes hereof to include tissue fragments, cell clumps and single cells. The process and product of this invention is suitable for preparing a wide variety of artificial tissues or organs prepared from single cells for insertion into the body. These cells can be fibroblasts, kidney cells, liver cells, thymus cells, thyroid cells, epidermal keratinocytes or cells from other tissues and organs. The process of this invention is particularly suitable for preparing artificial pancreatic endocrine tissue from pancreatic islets or islet cells for implantation into the body. This process can be used with any type of cell where implantation of the cells as an artificial tissue would be beneficial.

Insulin-dependent diabetes mellitus is a disorder resulting from lack of properly functioning pancreatic islet cells which normally produce and secrete insulin in response to glucose. For implanted cells to achieve a normal function in the body and secrete insulin in response to glucose, they may need to reproduce and reorganize to form a functioning cell grouping. The process and matrix of this invention is capable of allowing the requisite cell-to-cell contact, diffusion of nutrients and macromolecules for cell growth, and cell mobility for cellular reorganization to the functioning cell grouping required for formation of artificial organs and tissues. The optimal pancreatic islet cells for this function are substantially fibroblast-free cell preparations derived from culturing of fetal islet cells. For purposes of clarity of explanation and not by way of limitation, the invention will be described hereinafter in terms of pancreatic islet cells, it being understood that the process and matrix product is also suitable for implanting other types of cells including cells from adult tissues and organs, and that these other types of cells can be considered as alternates in the invention description.

The cell concentration in the solution determines, together with the concentration of matrix precursor, the cell density in the final matrix product. Solution cell densities can be from $10^2$ to $5 \times 10^8$ cells/ml. For matrices having low cell densities, the cell concentration in the solution can be from $10^2$ to $5 \times 10^5$ cells/ml, and for matrices having high cell densities, approaching the cell density of normal tissue, the cell concentration in the solution can be from $5 \times 10^5$ to $5 \times 10^8$ cells/ml.

Pancreatic islet cells suitable for incorporation into the matrix of this invention for implantation can be derived from pancreatic tissue by numerous published procedures or they can be derived from tissue, organ or cell cultures. The optimum pancreatic islet cells for implantation are believed to be fetal pancreatic proislet cells. These can be derived from the recipient species or they can be derived from a donor species which is different from the recipient species. When implanted into a suitable vascularized site in the body, held together with the matrix product of this invention, the cells differentiate to produce islet cells in a vascularized environment, an artificial endocrine pancreas, which responds to serum glucose by producing and secreting insulin. Procedures for preparing pancreas tissue for transplant are described by Lafferty, K. et al in *Transplantation Proceedings*. 14:714 (1984) and Lacy, P. et al in *Ann.Rev.Immunol*. 2:183 (1984).

The polymerization of the matrix precursor and reversible gel precursor is effected by ingredients and/or conditions of a second aqueous polymerization promotion solution with which the primary cell, matrix precursor, and gel precursor components are contacted. The ingredients of this second solution must be non-toxic, biocompatible, and must promote rapid polymerization of the matrix and reversible gel precursors in the primary solution.

The term "polymerization", for the purposes of this application, is defined to include any reaction by which soluble precursor materials are transformed to a shape-retaining, insoluble form, including chain formation, increase in chain length, and covalent or non-covalent cross-linking.

Preferred polymerization promoters include multivalent ions in solution which can form a salt with the acidic gums. The optimum ion is a physiologically compatible ion such as calcium in a concentration which provides in the mixture of the first and second solution, a calcium ion concentration which promotes rapid polymerization of the gel polymer precursor.

The first aqueous solution is contacted with the second aqueous solution in a manner which yields the desired solid matrix shape and size. For the production of spheres, the primary solution can be dripped or blown under air pressure into the secondary solution, the drop size being selected to yield the desired particle size. Alternatively, the two solutions can be quickly mixed and the mixture placed in a cavity having the general configuration of the desired product. A distribution of particles can be obtained with certain gel precursors by subjecting the secondary mixture to agitation while the primary solution is rapidly poured into the secondary solution.

The mixture is maintained until solidification of the gel precursor occurs. For optimal control of particle size and shape, this solidification should occur very rapidly. Gel polymer formation should occur in less than 10 minutes, preferably in less than one minute and optimally in less than 10 seconds. Such solidification is more or less temperature dependent, the degree of dependence varying with the characteristics of the selected gel precursor and gel polymerization promoter. The temperature dependence of solidification is preferably such that rapid solidification occurs at a temperature which, is compatible with cell physiology, i,e., from 0 to 50° C., preferably from 4° to 45° C. and optimally from 6° to 37° C.

Matrix precursor polymerization is initiated by contact with a matrix polymerization promoter (or promoting condition), the promoter being present in either the first or second aqueous solution. Matrix polymerization should occur at a rate which does not interfere with adequate gel polymerization. The polymerization rate is dependent upon the relative concentrations of matrix precursor and matrix polymerization promoter. The rate can be adjusted by adjusting the concentration of one or both concentrations. Matrix precursor polymerization should occur in from one minute to 24 hours. The optimal rate is determined by the physical and chemical characteristics of the particular reaction involved and the effect of the total environment during polymerization on the particular cell type being used. Preferably, the polymerization should occur in from 2 minutes to 10 hours and optimally in from 5 to 200 minutes.

The matrix solids comprising polymerized matrix precursor, gelled reversible gel precursor and cells are then removed from the solution mixture. In a preferred procedure, the matrix solids are then placed into a physiologically compatible solution such as described above. This solution can contain sufficient quantities of matrix polymerization promoting agents to initiate or continue the matrix polymerization if such promoting agents were not present in either the first or second aqueous solution. During this phase, contraction of the matrix structure may continue, and the cells may be brought into closer proximity.

After matrix polymerization sufficient to provide a matrix integrity which will retain pores after removal of the gel polymer has been achieved, the solid matrices are removed from the polymerization solution. They are preferably rinsed to remove residual solution containing the polymerization promoting agent. A suitable rinse solution is an isotonic solution, isotonic saline, or tissue culture medium as described hereinabove.

The solid matrices are then placed into a gel polymer dissolution promoting solution. The gel polymer dissolution promoting solution may contain nutrients required for maintaining viability of the cells and has suitable conditions, composition, or agents to reverse the polymerization reaction which produced the gel polymer. The solution should not contain any components which impair the integrity of the matrix structure or harm the cells. The solution preferably contains nutrients which maintain the viability of the cells. For pancreatic cells, the nutrients and nutrient media described above can be used.

For removing gel polymers of the polysaccharide type other than agarose, the solution should be devoid of multivalent ions, for when the cross-linked gel structures are exposed to a solution containing monovalent ions and is relatively deficient in multivalent ions, the multivalent ions are displaced in a reversable reaction by the monovalent ions. Preferably, removal of the multivalent ions during the depolymerization treatment is achieved by the use of sequestering agents or ion exchange resins having monovalent ions such as sodium ions in the exchange sites. Movement of the solution over the matrix surfaces promotes the gel dissolution, but excess agitation which damages the matrix structure or the cells should be avoided.

The solution preferably is maintained at a temperature of from 0° to 50° C. and preferably from 6° to 37° C. during this step. The matrix treatment is continued until the desired degree of porosity has been produced, that is, until the corresponding amount of the gel polymer has been dissolved and removed from the matrix structure. The time is temperature dependent and is generally from 5 to 60 minutes for temperatures within the range of from 6 to 37° C.

Agarose polymerization, being initiated by low solution temperatures, can be reversed by elevating the solution temperature. Agarose polymer dissolution temperatures can be from 37° to 65° C. and are preferably from 45° to 55° C. Alternatively, agarose polymers can be dissolved by treatment with an agarase solution.

The final porosity of the particles after gel polymer dissolution is dependent upon the initial concentration of the gel polymer in the particle, the degree of gel polymer crosslinking obtained, the degree of spatial contraction occurring during matrix polymerization, the amount of matrix crosslinking or contraction occurring after gel polymer dissolution, and other variables, including processing temperatures. These variables can affect average pore diameter, pore size distribution, average pore length, and total pore numbers. In the process and composition of this invention, pore diameters can be from $5 \times 10^{\times 3}$ to 40 microns, preferably from $2 \times 10^{-2}$ to 5 microns and optimally from 0.1 to 1 microns.

The final matrix is then recovered from the solution and placed in a nutrient medium such as those described above for maintaining the viability of the cells. The nutrient medium can be further supplemented with fetal calf serum or other conventional supplements. The nutrients required for maintenance and propogation of various cells are not a part of this invention, being well established and fully within the knowledge and skill of the person skilled in the art. For example, suitable media are described in READINGS IN MAMMALIAN CELL CULTURE. Robert Pollack (editor) second edition New York: Cold Spring Harbor Laboratory (1981) and other publications.

Further processing of the matrix to preserve or to expand or multiply the cells may be desirable, depending upon the cell type and factors involved in the insertion.

The matrix product of this invention can have a particle size as low as 0.02 mm in diameter and a size as large as 3 mm. The matrix product diameter is preferably from 0.05 to 1 mm and optimally from 0.1 to 0.3 mm. The matrix can have any desired cell density. For pancreatic islet cells, the cell density can range from $10^3$ to $5 \times 10^8$ cells/cc of matrix.

The matrix is porous and has a pore size sufficiently large to permit diffusion of nutrients and macromolecules to and from the cells entrapped in the matrix, and movement of cells.

The matrices of this invention can be implanted in the same manner as implantation of the corresponding tissue. For effective vascularization of the implanted matrix, the matrix is preferably implanted in a portion of the body which is not functionally affected by the implant and which will readily vascularize the implant. For example, if the matrix supports pancreatic islet cells, the matrix can be implanted in the mesenteric omentum, kidney subcapsular space, spleenic pulp, portal vein, and other sites appropriate for vascularization and function.

This invention is further illustrated by the following specific, but non-limiting examples. Unless otherwise specified, temperatures are given in degrees centigrade and concentrations are given as weight percents.

EXAMPLE 1

Monolayers of cultured pancreatic pre-islet cells were harvested by trypsinization and washed twice in isotonic, neutral pH buffer. The number of cells and percent viability were determined by trypan blue exclusion with a hemocytometer. Approximately $4 \times 10^6$ viable cells were recovered. The cells were maintained on ice and centrifuged ($150 \times g$) for 5 min before use. After removal of the supernatant, the cell pellet was recentrifuged ($200 \times g$) for 1 min to facilitate removal of residual interstitial liquid.

The following components (maintained on ice) were added to an isotonic saline solution in a separate 3 ml conical vial to give the component concentrations noted:

| Component | Concentration |
| --- | --- |
| Sodium alginate | 1.0% |
| Collagen, Type I | 0.05 mg/ml |
| Collagen, Type IV | 0.05 mg/ml |
| Fibronectin | 0.025 mg/ml |
| Lamanin | 0.025 mg/ml |

The solution was gently mixed and used to resuspend the cell pellet at $1 \times 10^7$ cells/ml. To this suspension were added fibrinogen (0.6 mg/ml final concentration) and thrombin (0.2 units/ml) to clot the fibrinogen. This final reaction mixture was rapidly aspirated into a syringe and expressed through the droplet-forming device as described in BIOMEDICAL APPLICATIONS OF MICROENCAPSULATION. F. Lim (editor) Boca Raton: CRC Press (1983) at a rate of 10 ml/hr. The air flow was set at a flowmeter reading of 50 psig. Droplets were delivered into 102 mM isotonic $CaCl_2$ for 2–10 min until the insoluble matrix formed. A series of washes in isotonic saline to remove $Ca^{+2}$ ions and/or free alginate were preformed, and the resulting particles were resuspended in RPMI 1640 containing 10% (v/v) fetal calf serum.

We claim:

1. A matrix composition comprising viable cells incorporated throughout a porous matrix of non-toxic biocompatible polymer substantially free from fibroblasts, said biocompatible polymer consisting essentially of the product of the polymerizations of a matrix polymer precursor and a reversible gel polymer, the matrix having a particle size of from 0.02 to 3 mm; a pore structure and size permitting cell movement throughout the matrix, movement of host cells into the matrix, diffusion of nutrients and macromolecules into and out of the matrix; wherein the composition is free from encapsulation in a semi-permeable membrane.

2. The matrix composition of claim 1 wherein the matrix is a product of the polymerization of a matrix polymer precursor selected from the group consisting of plasma, fibrinogen, casein, fibrin, limulus lysate, milk protein and collagen and mixtures thereof.

3. The matrix composition of claim 1 wherein the viable cells are pancreatic islet cells.

4. The matrix composition of claim 1 produced by
    (a) polymerizing polymer precursors in an aqueous solution containing a matrix polymer precursor, a reversible gel polymer precursor, and viable cells to form a shape retaining solid matrix comprising viable cells, matrix polymer and reversible gel polymer,
    (b) dissolving gel polymer and removing gel polymer dissolution products from the matrix, and
    (c) recovering an insoluble, porous, unencapsulated matrix containing viable cells, wherein the conditions and reagents are selected to not significantly impair the viability of the cells.

5. The matrix composition of claim 4 wherein the viable cells are pancreatic islet cells.

6. The matrix composition of claim 1 produced by
    (a) polymerizing polymers precursors in an aqueous solution containing a matrix polymer precursor, a reversible gel polymer precursor, and viable cells to form a shape retaining solid matrix comprising viable cells, matrix polymer and reversible gel polymer,
(i) wherein the matrix polymer precursor is selected from the group consisting of plasma, fibrinogen, casein, fibrin, limulus lysate, milk protein, collagen, and mixtures thereof, and
(ii) the reversible gel polymer precursor is a member selected from the group consisting of agarose, carrageenan, agar, alginate, guar gum, gum arabic, pectin, tragacanth gum, xanthan gum, and mixtures thereof,
(b) dissolving gel polymer and removing gel polymer dissolution products from the matrix, and
(c) recovering an insoluble, porous, unencapsulated matrix containing viable cells,
wherein the conditions and reagents are selected to not significantly impair the viability of the cells.

7. The matrix composition of claim 1 wherein the aqueous solution from which the matrix composition is formed contained fibronectin and laminin.

* * * * *